(12) United States Patent
Haines

(10) Patent No.: US 12,220,286 B2
(45) Date of Patent: Feb. 11, 2025

(54) COLORED CLOSING KIT

(71) Applicant: Medline Industries, LP, Northfield, IL (US)

(72) Inventor: Kimberly M. Haines, Ligonier, PA (US)

(73) Assignee: Medline Industries, LP, Northfield, IL (US)

( * ) Notice: Subject to any disclaimer, the term of this patent is extended or adjusted under 35 U.S.C. 154(b) by 489 days.

(21) Appl. No.: 17/677,916

(22) Filed: Feb. 22, 2022

(65) Prior Publication Data

US 2022/0175488 A1   Jun. 9, 2022

Related U.S. Application Data

(62) Division of application No. 16/053,775, filed on Aug. 2, 2018, now abandoned.

(60) Provisional application No. 62/552,974, filed on Aug. 31, 2017.

(51) Int. Cl.
| | |
|---|---|
| *A61B 90/92* | (2016.01) |
| *A61B 42/10* | (2016.01) |
| *A61B 46/00* | (2016.01) |
| *A61B 50/00* | (2016.01) |
| *A61B 50/30* | (2016.01) |

(52) U.S. Cl.
CPC .............. *A61B 90/92* (2016.02); *A61B 50/00* (2016.02); *A61B 50/30* (2016.02); *A61B 42/10* (2016.02); *A61B 46/00* (2016.02)

(58) Field of Classification Search
CPC ......... A61B 90/92; A61B 50/00; A61B 50/30; A61B 42/10; A61B 46/00
See application file for complete search history.

(56) References Cited

U.S. PATENT DOCUMENTS

| | | | |
|---|---|---|---|
| 2,734,543 A | 2/1956 | Hunter | |
| 4,705,171 A | 11/1987 | Eldridge | |
| 4,844,259 A | 7/1989 | Glowczewskie, Jr. | |
| 5,573,529 A * | 11/1996 | Haak ..................... | A61B 90/92 606/1 |
| 6,460,702 B2 | 10/2002 | Hammond | |
| D480,816 S | 10/2003 | McMichael | |
| D483,487 S | 12/2003 | Harding | |
| 7,802,313 B2 | 9/2010 | Czajka | |

(Continued)

OTHER PUBLICATIONS

Disposable Sterile Universal Surgical Packs, posted at lantianmedical. com, available Oct. 2, 2018, online, URL:https://web.archive.org/ web/20181002215531 /http://www.lantianmedical.com/products/ surgical-pack/disposable-sterile-universal-surgical-packs. html (Year: 2018).

(Continued)

*Primary Examiner* — Matthew Mikels

(74) *Attorney, Agent, or Firm* — Fitch, Even, Tabin & Flannery LLP

(57) ABSTRACT

A surgical collection having a primary surgical kit, the primary surgical kit comprising at least one first surgical implement and a primary wrap, the primary wrap comprising a first visible coding; a secondary surgical kit, the secondary surgical kit comprising at least one second surgical implement and a secondary wrap, the secondary wrap comprising a second visible coding; and an outer wrap, wherein the primary surgical kit and the secondary surgical kit are at least partially contained within the outer wrap.

11 Claims, 5 Drawing Sheets

(56) References Cited

U.S. PATENT DOCUMENTS

| | | |
|---|---|---|
| D634,214 S | 3/2011 | Janssen |
| 7,914,519 B2 | 3/2011 | Moran |
| 8,246,605 B2 | 8/2012 | Valaie |
| D673,674 S | 1/2013 | Ho |
| 8,371,306 B2 | 2/2013 | Haines |
| 8,390,452 B2 | 3/2013 | Blake |
| D682,423 S | 5/2013 | Becker |
| 8,435,210 B2 | 5/2013 | Zinger |
| 8,448,786 B2 | 5/2013 | Tomes |
| D687,542 S | 8/2013 | Esposito |
| D694,424 S | 11/2013 | Kwak |
| 8,657,800 B2 | 2/2014 | Ho |
| 8,678,190 B2 | 3/2014 | Tomes |
| 8,777,930 B2 | 7/2014 | Swisher |
| D720,471 S | 12/2014 | Angel |
| 8,919,554 B2 | 12/2014 | Huldin |
| D736,924 S | 8/2015 | Oberlaender |
| 9,168,107 B2 | 10/2015 | Khajavi |
| 9,517,870 B2 | 12/2016 | Lien |
| D779,082 S | 2/2017 | Andre |
| D784,556 S | 4/2017 | Alden |
| D838,999 S | 1/2019 | Gandhi |
| D849,936 S | 5/2019 | Allard |
| D849,937 S | 5/2019 | Whitaker |
| 2002/0017328 A1 | 2/2002 | Loo |
| 2003/0153897 A1 | 8/2003 | Russo |
| 2006/0244597 A1 | 11/2006 | Tethrake |
| 2008/0124674 A1 | 5/2008 | Meuchel |
| 2009/0188826 A1 | 7/2009 | Porteous |
| 2010/0274205 A1 | 10/2010 | Morelli |
| 2013/0240399 A1 | 9/2013 | Czajka |
| 2017/0368302 A1 | 12/2017 | Brooks |
| 2018/0228998 A1 | 8/2018 | Anderson |
| 2019/0060030 A1 | 2/2019 | Haines |

OTHER PUBLICATIONS

Erase SSI Solutions for Surgical Site Infections, Intra-Operative Color-Coded, Sterilized Surgical Closure Kit, posted at medline.com, no posting date available, online, URL:https://www.medline.com/pages/clinical-expertise/infection-prevention/erase-ssi-surgical-site-infection-solution/ (Year: 2019) (Year: 2019).

Haines; U.S. Appl. No. 16/053,775, filed Aug. 2, 2018.

How to Wrap a Veterinary Surgical Pack, posted at instructables.com, no posting date, online, URL: https://www.instructables.com/id/How-to-Wrap-a-Veterinary-Surgical-Pack/ (Year: 2019).

Medical Assistant Training Prepare for Minor Surgical Procedures, posted at youtube.com on Dec. 19, 2010, online, URL:https://www.youtube.com/watch?v=-ggM1sTpYaM (Year: 2010).

Premium Freezer Paper Helps Preserve Deer Meat Freshness Longer, posted at oren-intl.com, posted Jan. 8, 2013, online, URL:http://www.oren-intl.com/blog/bld/256784/Premium-Freezer-Paper-Helps-Preserve-Deer-Meat-Freshness-Longer (Year: 2013) (Year: 2013).

Survival Surgery procedures: Large Animals, posted at web.jhu.edu, available Jan. 11, 2015, online, URL:https://web.archive.org/web/20150111213051/http://web.jhu.edu/animalcare/procedures/survival-large.html (Year: 2015).

USPTO; Final Office Action issued in U.S. Appl. No. 16/053,775 mailed Nov. 19. 2021.

USPTO; Non-Final Office Action issued in U.S. Appl. No. 16/053,775 mailed May 17, 2021.

* cited by examiner

COLORED CLOSING KIT

This application is a divisional of U.S. application Ser. No. 16/053,775, filed Aug. 2, 2018, for COLORED CLOSING KIT, which claims the benefit of U.S. Provisional Application No. 62/552,974, filed Aug. 31, 2017, for COLORED CLOSING KIT, which are incorporated in their entirety herein by reference.

BACKGROUND OF THE INVENTION

In a typical surgical procedure, dozens or hundreds of surgical implements may be used, these including such implements as needles, knife blades, safety pins, scalpels, clamps, scissors, sponges, towels, electrosurgical adapters, tweezers, forceps, suction tips and tubes, scopes, ultrasound tissue disruptors, aseptic bulbs, cryotomes and cutting laser guides, and measuring devices, among hundreds of other such implements. The risks of inadvertently leaving a surgical implement behind in the patient, a condition known as gossypiboma, is well known.

Many studies have taken place to pinpoint the causes of gossypiboma. It is believed that human factors such as exhaustion, lack of tools necessary to aid in producing an accurate count, and a chaotic environment all have been seen to increase the risk of forgetting a tool. In particular, inaccurate tool counts are a main reason why surgical implements can be left behind. An inaccurate count can occur when surgeons and surgical staff are rotated out during lengthy surgical procedures and when a separate surgical team is used to close the surgical wound following the primary surgical procedure.

Now, it has been found that a closing kit may be provided in addition to a primary surgical kit, the closing kit and primary surgical kit having at least one surgical implement that are of different colors. Ideally, most or all of the implements in the primary surgical kit, such as sponges, wipes, and the like are of one color, and most or all of the implements in the closing kit are of the second color, and the kits are further provided with gowns and gloves of the respective color. The closing kit may be provided as part of a surgical collection that is bound by a wrap that is of the second color. After performing a surgical procedure on a patient employing the primary surgical kit, the primary surgical kit is inventoried, then removed from the surgical area. The closing kit then is employed to perform a closing procedure. After closing, the closing kit is inventoried. The use of separately colored primary surgical and closing kits is believed to assist in preventing confusion between the primary surgical phase and the closing phase, particularly if separate teams are employed.

SUMMARY

In accordance with one embodiment, the present description comprises a surgical method comprising providing a primary surgical kit comprising at least one first surgical implement for a particular surgical procedure, the at least one first surgical implement being of a first visible coding; providing a secondary surgical kit comprising at least one second surgical implement, the at least one second surgical implement being of a second visible coding; performing the particular surgical procedure on a patient employing the primary surgical kit; inventorying the primary surgical kit following the performing of the particular surgical procedure; removing the primary surgical kit from an area proximate to the patient; performing a second surgical procedure on the patient using the secondary surgical kit; and inventorying the secondary surgical kit following the performing of the second surgical procedure.

In accordance with another embodiment, the present description comprises a surgical collection comprising a primary surgical kit, the primary surgical kit comprising at least one first surgical implement and a primary wrap, the primary wrap comprising a first visible coding; contained within the primary surgical kit, a secondary surgical kit, the secondary surgical kit comprising at least one second surgical implement and a secondary wrap, the secondary wrap comprising a second visible coding.

In accordance with a further embodiment, the present description comprises a surgical collection comprising a primary surgical kit, the primary surgical kit comprising at least one first surgical implement and a primary wrap, the primary wrap comprising a first visible coding; a secondary surgical kit, the secondary surgical kit comprising at least one second surgical implement and a secondary wrap, the secondary wrap comprising a second visible coding; and an outer wrap, wherein the primary surgical kit and the secondary surgical kit are at least partially contained within the outer wrap.

Figure 1:
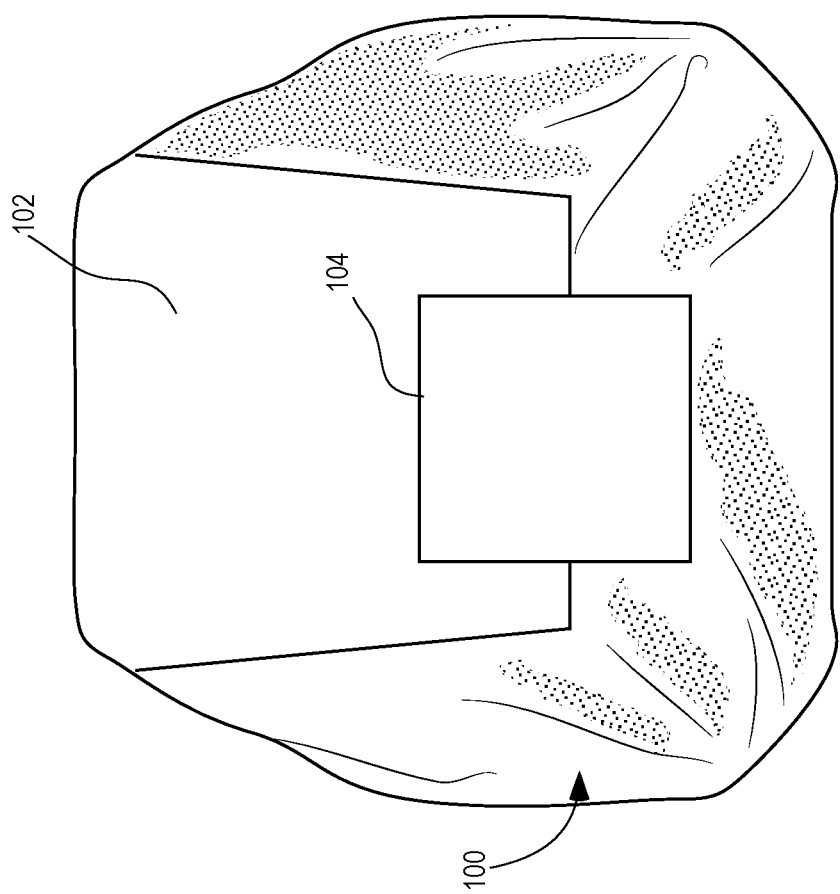
FIG. 1 is a top perspective view of a surgical collection in accordance with one embodiment.

Corresponding reference characters indicate corresponding components throughout the several views of the drawings. Skilled artisans will appreciate that elements in the figures are illustrated for simplicity and clarity and have not necessarily been drawn to scale. For example, the dimensions of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention.

DETAILED DESCRIPTION

Figure 2:
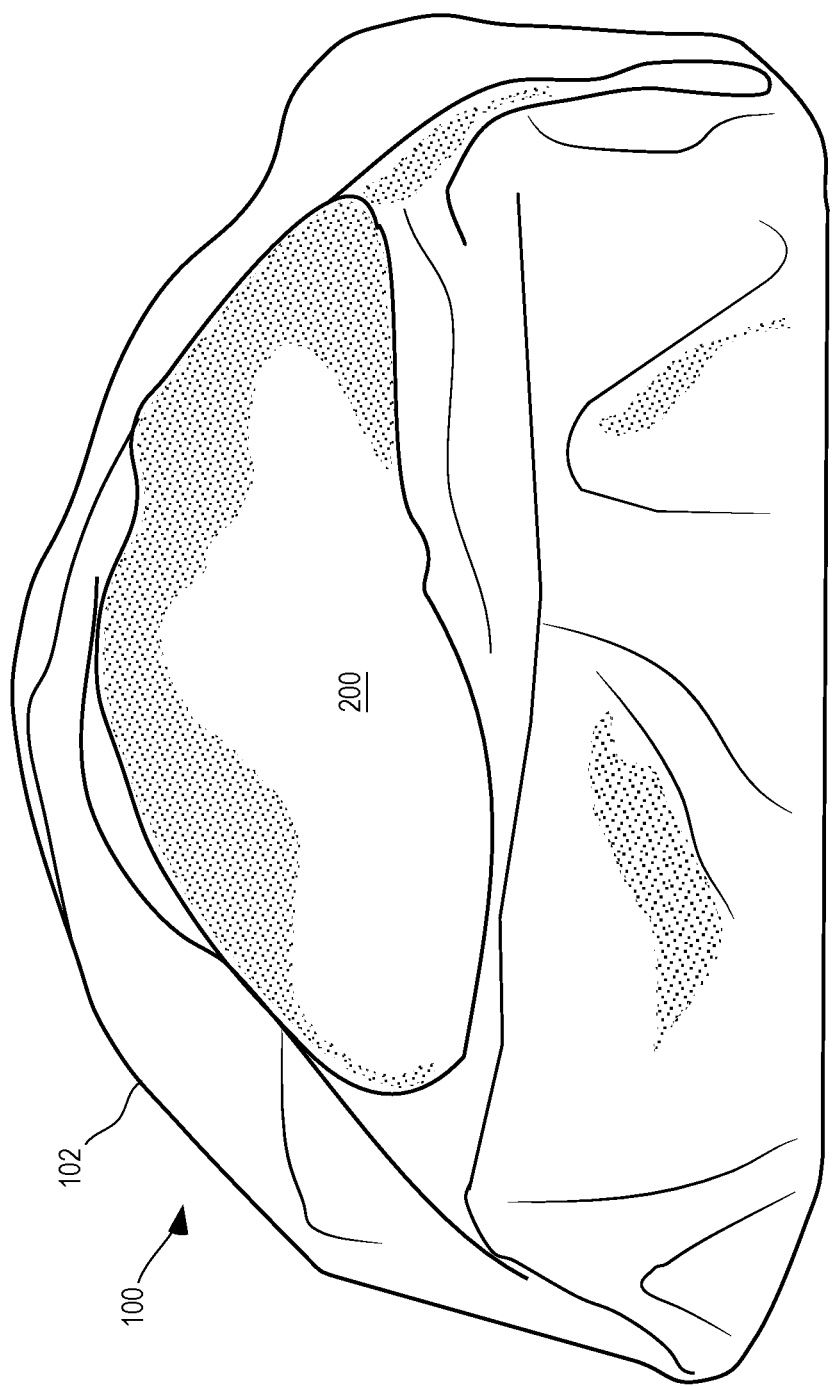
FIG. 2 is a first side perspective view of the surgical collection of FIG. 1.
Figure 3:
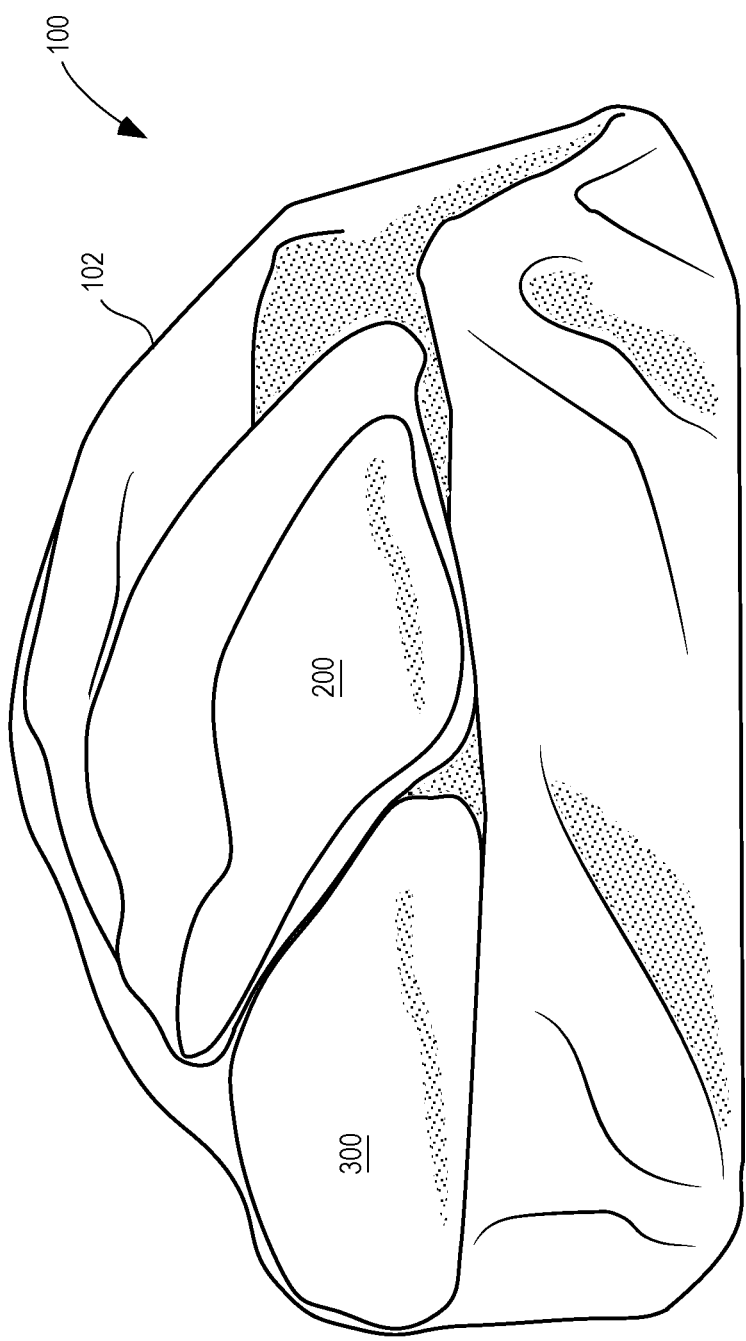
FIG. 3 is a second side perspective view of a master kit for a surgical procedure in accordance with the embodiment of FIG. 1.

Referring to FIG. 1, a top perspective view is shown of a surgical collection, or master kit 100 for a surgical procedure in accordance with one embodiment. Shown is the master kit 100, the outer wrap 102 and a seal 104. As seen in FIGS. 1, 2 and 3, the outer wrap 102 envelops or at least partially contains the closing kit 200. The outer wrap and many of the implements in the primary surgical kit may have one color (e.g. blue) and the wrap and implements of the closing kit may have a different color (e.g. green).

Various embodiments of the present invention mitigate against retained surgical tools and other implements by facilitating the division of the entire surgical process into stages with distinct kits of surgical implements designated for each phase (or stage) of a surgical procedure. During each stage of the surgical procedure, a stage-specific surgical kit containing each of the surgical implements for the stage of the surgical procedure is utilized, as opposed to a single surgical kit containing, for example, all of the surgical implements needed for the entire surgical procedure.

The contents of the distinct kits are contained (or enveloped) within an exterior wrap. Each of the exterior wraps of the distinct kits are color-coded in a distinct contrasting color, such as for example red, blue, green, yellow, orange, violet, white, black and gray, or otherwise visually coded, such as by the use of printed patterns, such as striping, stippling, cross-hatching, and the like across the entire visible portion of an exterior wrap or package of the distinct kits. Distinct contrasting colors or other visual coding (or visual indicia) covering the visible portion of the exterior wrap can cover, for example, more than thirty (30) percent of the visible portion of the outer wrap 102.

The distinct kits may be contained (or enveloped) within an outer wrap 102 that contains all of the implements for the entire surgical procedure forming a master kit 100. Additionally, surgical implements outside of the distinct kits may be contained within the outer wrap 102, such as for example surgical implements for site preparation, whereas the distinct kits may be for, for example, an opening procedure, a primary procedure and/or a closing procedure. The outer wrap 102 also may have a distinct contrasting color or otherwise visually coded. Distinct contrasting colors or other visual coding (or visual indicia) covering the visible portion of the outer wrap 102, for example, covering more than thirty (30) percent of the visible portion of the exterior wrap.

Figure 4:
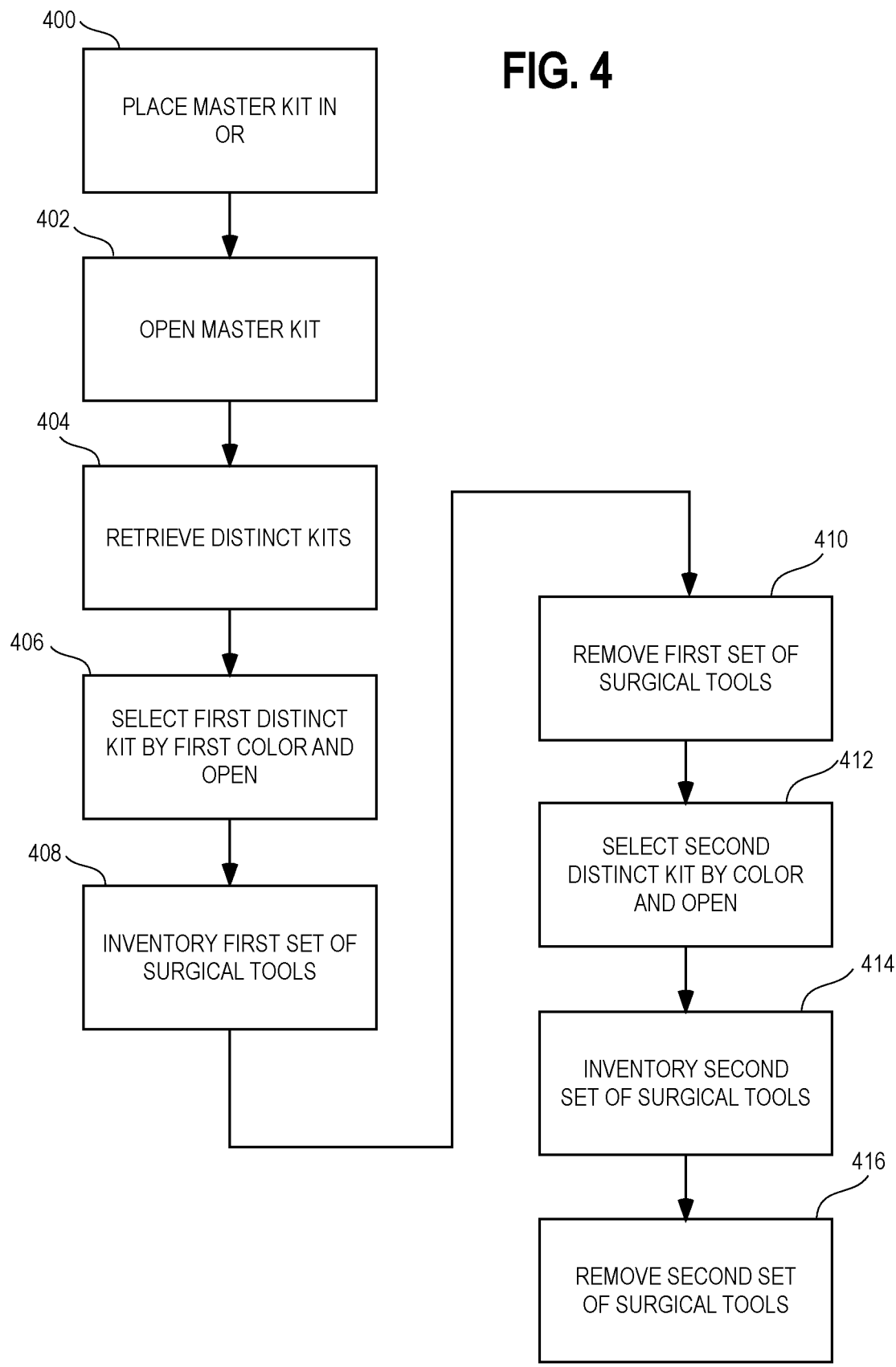
FIG. 4 is a flow chart of a process for using a master kit, and a plurality of distinct kits for a surgical procedure in accordance with the embodiment of FIG. 1

Referring to FIG. 4, a flow chart is shown of a process for using a master kit 100, and a plurality of distinct kits for a surgical procedure in accordance with the embodiment of FIG. 1.

In practice, a surgical staff member will transport the master kit 100 into the operating room in step 400, open the outer wrap 102 in step 402 and remove the closing kit in step 404 for each stage of the surgical procedure. The outer wrap 102 may be disposed of or may serve a second function during the surgical procedure, for example, as a disposable cloth or operating room (OR) sheet or drape.

At the outset of each stage of the surgical procedure, the distinct kit for the stage of the surgical procedure is selected by distinct contrasting color in step 406 and is unpacked by opening the exterior wrap in step 406 of the distinct kit for the stage and removing the surgical implements for the stage from the distinct kit for the stage. The exterior wrap may be retained to collect the surgical implements of the distinct kit following the stage. Alternatively, the exterior wrap may be disposed of or may serve a second function during the surgical procedure, for example, as a disposable cloth or operating room (OR) sheet or drape.

Selection of the distinct kit for the stage is facilitated in that surgical personnel are able to quickly identify the appropriate distinct kit 200 by its distinct contrasting color, thereby distinguishing the appropriate distinct kit for the stage from other distinct kits for other stages.

Following completion of each stage, the surgical implements are removed in step 410 from the proximity of the patient on whom the surgical procedure is being performed.

An inventory is performed in step 408 at the end of each stage (either before or after the removal in Step 410) in order to assure that, for example, as different teams of surgical staff are brought into the surgical procedure at each stage no surgical tools are retained within the patient. Thus, an inventory is performed before new surgical staff and new surgical implements are introduced into proximity of the patient.

Once the primary surgical procedure is completed, an inventory in step 408 is performed by the first surgical team of the primary surgical stage in order to assure that all of the surgical implements for the primary surgical stage have been removed from the proximity of the patient, and specifically to assure that the surgical implements for the primary surgical stage are not retained within the patient.

Then, the second team of surgical staff enters proximity to the patient to perform the closing stage procedure. This second surgical team would utilize a distinct closing kit 200 contained within an exterior wrap having a second distinct contrasting color, for example, black, in order to distinguish it from the primary surgical kit used by the first surgical team in the primary surgical stage. The distinct kit 200 for the closing stage is selected by distinct contrasting color in step 412 and is unpacked by opening the exterior wrap in step 412. As above, the exterior wrap may be retained to collect the surgical implements of the closing kit 200 following the stage. Alternatively, the exterior wrap may be disposed of or may serve a second function during the surgical procedure, for example, as a disposable cloth or operating room (OR) sheet or drape.

Once the closing procedure is completed, an inventory is performed in step 414 by the second surgical team of the closing stage and the surgical implements are removed from the proximity of the patient in step 416. In this way, it is assured that all of the surgical implements for the closing stage have been inventoried and removed from the proximity of the patient, and specifically to assure that the surgical implements for the closing surgical stage are not retained within the patient.

In this way, in accordance with the present embodiments, the risk of retained surgical implements within the patient is substantially mitigated in that each distinct kit 200, 300 is utilized by preferably a single team of surgical staff, and is clearly visually distinguished from surgical kits utilized by other teams of surgical staff by distinct contrasting colors or other visual indicia covering the visible portion of the exterior wrap, for example, covering more than thirty (30) percent of the visible portion of the exterior wrap.

Figure 5:
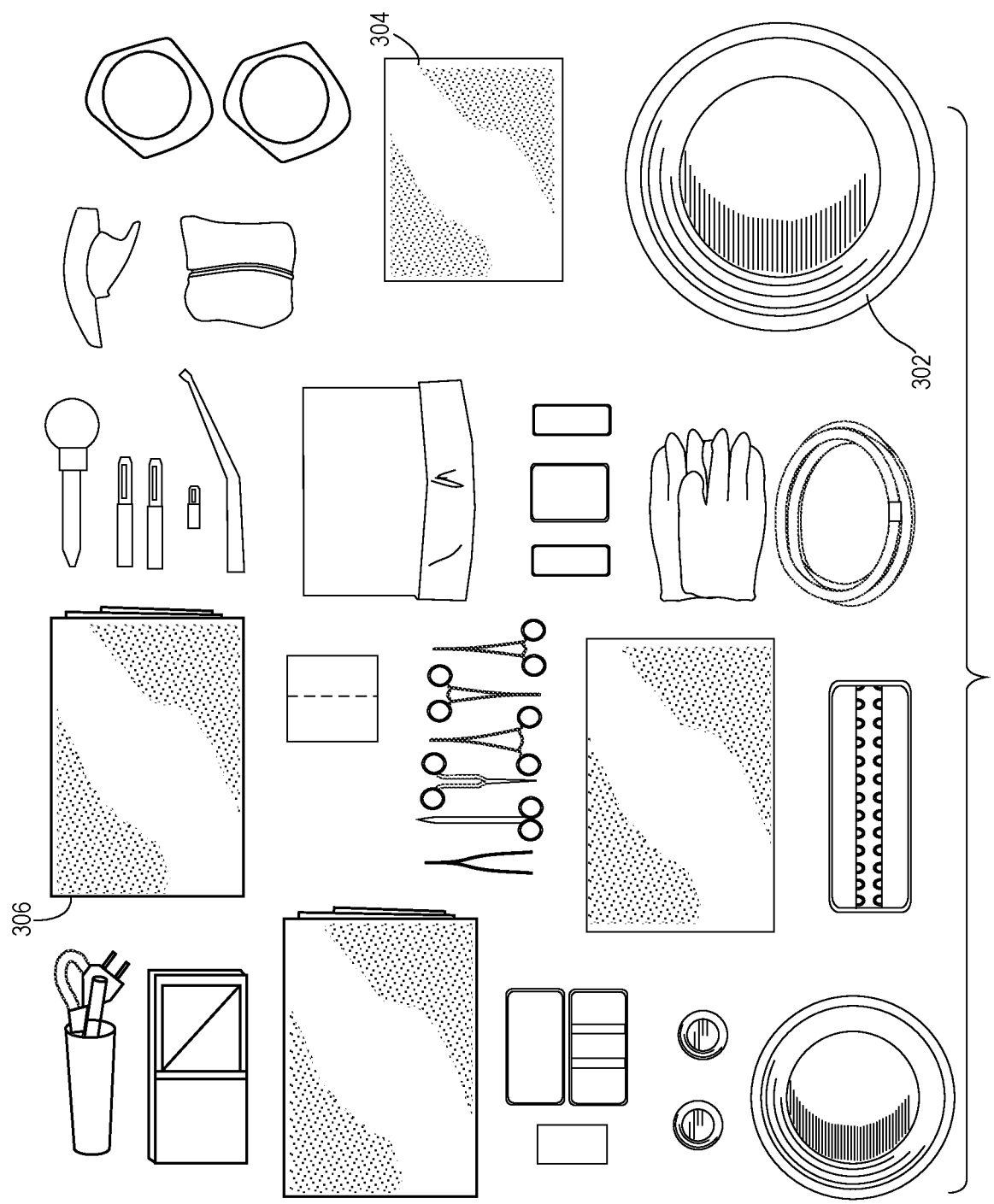
FIG. 5 is a photograph of a representative closing kit.

Any suitable implements may be provided with the primary surgical kit and the closing kit and any other kits in the master kit. For example, with respect to the kit 200 illustrated in FIG. 1, as seen in FIG. 5 the kit may include a basin 302, wrap 304, and stand cover 306, among other implements.

While the invention herein disclosed has been described by means of specific embodiments, examples and applications thereof, numerous modifications and variations could be made thereto by those skilled in the art without departing from the scope of the invention set forth in the claims.

All methods described herein can be performed in any suitable order unless otherwise indicated herein or otherwise clearly contradicted by context. The use of any and all examples, or language describing an example (e.g., "such as") provided herein, is intended to illuminate the invention and does not pose a limitation on the scope of the invention. Any statement herein as to the nature or benefits of the invention or of the preferred embodiments is not intended to be limiting. This invention includes all modifications and equivalents of the subject matter recited herein as permitted by applicable law. Moreover, any combination of the above-described elements in all possible variations thereof is encompassed by the invention unless otherwise indicated herein or otherwise clearly contradicted by context. The description herein of any reference or patent, even if identified as "prior," is not intended to constitute a concession that such reference or patent is available as prior art against the present invention. No unclaimed language should be deemed to limit the invention in scope. Any statements or suggestions herein that certain features constitute a component of the claimed invention are not intended to be limiting unless reflected in the appended claims. Neither the marking of the patent number on any product nor the identification of the patent number in connection with any service should be deemed a representation that all embodiments described herein are incorporated into such product or service.

What is claimed is:

1. A surgical method comprising:
providing a primary surgical kit comprising at least one first surgical implement for a particular surgical procedure, the at least one first surgical implement being of a first visible coding;
providing a secondary surgical kit comprising at least one second surgical implement, the at least one second surgical implement being of a second visible coding;
performing the particular surgical procedure on a patient employing the primary surgical kit;
inventorying the primary surgical kit following the performing of the particular surgical procedure;
removing the primary surgical kit from an area proximate to the patient;
performing a second surgical procedure on the patient using the secondary surgical kit; and
inventorying the secondary surgical kit following the performing of the second surgical procedure,
further comprising:
opening a master kit comprising at least one additional surgical implement outside said primary surgical kit and outside said secondary surgical kit, said opening said master kit comprising removing an outer wrap comprising a surgical drape.

2. The surgical method of claim 1 comprising:
providing said primary surgical kit comprising said first visible coding, wherein said first visible coding is a first color; and
providing said secondary surgical kit comprising said second visible coding, wherein said second visible coding is a second color.

3. The surgical method of claim 1 comprising:
providing said primary surgical kit comprising said first visible coding, wherein said first visible coding is a first printed pattern; and
providing said secondary surgical kit comprising said second visible coding, wherein said second visible coding is a second printed pattern.

4. The surgical method of claim 3, comprising:
completing a preparation of a surgical site for said particular surgical procedure using said at least one additional surgical implement prior to said performing said particular surgical procedure on said patient.

5. The surgical method of claim 4 comprising:
inventorying said at least one additional surgical implement and removing said at least one additional surgical implement from proximity of said patient prior to said performing said particular surgical procedure on said patient.

6. The surgical method of claim 1 comprising:
said performing said second surgical procedure on said patient using said secondary surgical kit comprising completing a closing procedure.

7. A surgical method comprising:
providing a primary surgical kit comprising at least one first surgical implement for a particular surgical procedure, the at least one first surgical implement being of a first visible coding;
providing a secondary surgical kit comprising at least one second surgical implement, the at least one second surgical implement being of a second visible coding;
performing the particular surgical procedure on a patient employing the primary surgical kit;
inventorying the primary surgical kit following the performing of the particular surgical procedure;
removing the primary surgical kit from an area proximate to the patient; performing a second surgical procedure on the patient using the secondary surgical kit; and
inventorying the secondary surgical kit following the performing of the second surgical procedure,
further comprising:
opening a master kit comprising at least one additional surgical implement outside said primary surgical kit and outside said secondary surgical kit, and
completing a preparation of a surgical site for said particular surgical procedure using said at least one additional surgical implement prior to said performing said particular surgical procedure on said patient.

8. The surgical method of claim 7 comprising:
providing said primary surgical kit comprising said first visible coding, wherein said first visible coding is a first color; and
providing said secondary surgical kit comprising said second visible coding, wherein said second visible coding is a second color.

9. The surgical method of claim 7 comprising:
providing said primary surgical kit comprising said first visible coding, wherein said first visible coding is a first printed pattern; and
providing said secondary surgical kit comprising said second visible coding, wherein said second visible coding is a second printed pattern.

10. The surgical method of claim 7 comprising:
inventorying said at least one additional surgical implement and removing said at least one additional surgical implement from proximity of said patient prior to said performing said particular surgical procedure on said patient.

11. The surgical method of claim 7 comprising:
said performing said second surgical procedure on said patient using said secondary surgical kit comprising completing a closing procedure.

* * * * *